United States Patent [19]

Deardorff

[11] Patent Number: 4,788,172
[45] Date of Patent: Nov. 29, 1988

[54] TITANIUM COMPOUNDS

[76] Inventor: Donald L. Deardorff, P.O. Box 853, East Greenwich, R.I. 02818

[21] Appl. No.: 77,905

[22] Filed: Jul. 27, 1987

[51] Int. Cl.$^4$ ............................................. B01J 31/02
[52] U.S. Cl. .................................. 502/167; 502/171; 556/54; 556/56
[58] Field of Search ................... 502/167, 171; 556/54, 556/56

[56] References Cited

U.S. PATENT DOCUMENTS

| | | | |
|---|---|---|---|
| 2,621,193 | 12/1952 | Langkammerer | 260/414 |
| 2,621,194 | 12/1952 | Balthis | 260/414 |
| 2,621,195 | 12/1952 | Haslam | 260/414 |
| 2,643,262 | 6/1953 | Bostwick | 528/395 |
| 2,727,881 | 12/1955 | Caldwell et al. | 528/279 |
| 2,824,114 | 2/1958 | Bostwick | 556/56 |
| 2,824,115 | 2/1958 | Beacham et al. | 556/56 |
| 2,935,522 | 5/1960 | Samour | 556/56 |
| 3,056,817 | 10/1962 | Werber et al. | 560/99 X |
| 3,056,818 | 10/1962 | Werber | 560/99 X |
| 3,892,791 | 7/1975 | Brook et al. | 556/56 |
| 4,007,218 | 2/1977 | Ghanayem et al. | 560/99 |
| 4,020,010 | 4/1977 | Vogt et al. | 502/170 |
| 4,159,209 | 6/1979 | Womersley | 106/308 |
| 4,216,337 | 8/1980 | Baba et al. | 560/78 |
| 4,260,735 | 4/1981 | Bander et al. | 528/279 |
| 4,284,793 | 8/1981 | Sagara et al. | 560/78 |
| 4,506,091 | 3/1985 | Deardorff | 560/99 |
| 4,526,725 | 7/1985 | Deardorff | 556/56 |

FOREIGN PATENT DOCUMENTS

| | | | |
|---|---|---|---|
| 970431 | 9/1964 | United Kingdom . | |
| 1058242 | 2/1967 | United Kingdom | 560/99 |

OTHER PUBLICATIONS

Tyzor Organic Titanates, DuPont Co., Product Bulletin E-60136 10/83, pp. 16–17.
Titanic Acid Esters/Organic Titanates, Kay-Fries, Inc., Montvale, N.J., Table 1.
Tilcom Organic Titanates, Product Bulletin TIL 11A, TIL Div., Tioxide UK Ltd, Tioxide America Inc., Columbia, Md., pp. 36–43.

Primary Examiner—Patrick P. Garvin
Attorney, Agent, or Firm—Barlow & Barlow Ltd.

[57] ABSTRACT

New compositions and methods of preparing hydrolyzed titanium chelates are disclosed. New chelates of tetra-isopropyl titanate with alkanolamines in 1/1 mole ratios have high activity as catalysts and exhibit surprising chemical characteristics as reactive intermediates. New partially hydrolized chelates are water soluble, chemically reactive and highly active as esterification catalysts.

5 Claims, No Drawings

TITANIUM COMPOUNDS

BACKGROUND AND SUMMARY OF THE INVENTION

Titanium alkoxides and chelates of titanium alkoxides are well known and have broad industrial application. But the chemistry of these compounds is complex and often is not well understood. In some instances this has limited the use of titanium in an application, and catalysis of ester manufacture is one of those instances. This invention is concerned with advancing the chemical technology of titanium chelates and esterification catalysis.

Since 1950 the catalyst characteristics of titanium compounds, as well as those of tin, antimony and other organometallics were widely investigated as demonstrated by U.S. Pat. No. 3,254,959. While the earliest focus of such work was on organometallic catalysis of high temperature polyesterifications (see British Specification No. 1,246,346), the use of tetraisopropyl titanate catalysis in manufacture of plasticizer esters became commercially important soon after its disclosure in the Werber patents, U.S. Pat. Nos. 3,056,817 and 3,056,818. These patents demonstrate the utility of titanium alkoxides at temperatures above 200° C. and cite important advantages in less degrading of alcohols and refining to high purity esters without caustic wash. Similar disclosures for titanic acid appear in U.S. Pat. No. 2,727,881 and in British Pat. No. 1,058.242 and a variety of titanium and tin compounds have been disclosed in U.S. Pat. Nos. 3,254,959; 4,020,010; 4,260,735; and in British Pat. No. 1,246,346 with potential advantages of faster reactions and the avoiding of undesirable side effects in both general purpose and polymeric esters.

Disadvantages associated with titanium catalysis are well known and are the subject of several patents. The largest disadvantage of titanium is the high temperature range of 200°-220° C. required for practical reaction rates. Synthesis of organometallic catalysts with increased activity has been the object of many investigations. Combinations of titanates and tin salts are proposed by Vogt in U.S. Pat. No. 4,020,010 as more active than the individual components. A number of workers have disclosed methods to avoid the increase in acidity during steam distillation and the disadvantages of washing in refining processes. Treatment with solid bases to avoid these problems is described by Chilton in U.S. Pat. No. 3,818,071, Ghanayem in U.S. Pat. No. 4,007,218 and Sagara in U.S. Pat. No. 4,284,793, while an intricate heat treatment and filtration process is described in a recent U.S. Pat. No. 4,216,337 by Baba. In U.S. Pat. Nos. 4,506,091 and 4,526,725 that are related to the instant invention, there is disclosed the use of chelating agents to assist in the removal of titanium residues from the reaction mixture, and to make alkoxy titanium chelates that show higher catalytic activity and are more easily removed from the ester in the refining process. Fully chelated titanium compounds are well known and are valuable commercial compounds, reference for which may be found in Kirk-Othmer, *Encyclopedia of Chemical Technology*, Vol. 23 3rd Ed. 1983, John Wiley & Sons, New York, N.Y. and Field & Case, *The Organic Chemistry of Titanium*, 1965, Butterworths. The use of titanium triethanolamine chelate (Tyzor TE) is known and exhibits a lower order of activity in comparison with alkoxy titanates. As disclosed in U.S. Pat. No. 4,260,735, the use of TE is reported to have advantange in retarding formation of ether by-products in catalysis of certain polymeric esters.

From a commercial view the use of titanium compounds in ester catalysis has been limited to the alkoxy titanates TPT and TBT for the most part. Notable exceptions are the applications of TE, mentioned above, and the very recent introduction and use of Tyzor GR, an alkoxy titanium chelate based on the disclosure in U.S. Pat. No. 4,526,725.

This invention discloses new titanium chelate compositions that provide both improved catalysts for ester manufacture and advantage of insight to the nature and fate of the catalyst.

Compositions of the invention include chelates that are derived from tetra-alkyl titanates and dialkanolamines as well as certain hydrolysis products of the chelates so derived.

In Deardorff U.S. Pat. No. 4,506,091, there is described the use of chelating agents for the treatment of titanium catalyzed reaction mixtures, the agents being added prior to steam distillation and assisting in making the hydrolysis and precipitation of catalyst residues efficient and without increase of acid value; giving high purity esters in only a further filtration step, and avoiding the caustic and water wash usually required to get equivalent results.

In Deardorf patent, U.S. Pat. No. 4,526,725, there is described the use of chelating agents to make alkoxy titanium chelate (ATC) compositions that are improved catalysts for ester manufacture. These compositions, which include alkyl groups with more than three carbon atoms to lower water sensitivity, provide advantages in refining as well as a surprising enhancement in catalytic activity.

By these disclosures there is provided compositions and methods that are highly effective to avoid certain problems that are common to ester manufacture. But it is evident that further improvements in reaction rate and process design might be made if one had better insight of the process chemistry. This invention is concerned with the discovery of new information related to the structure and the fate of catalyst species, and of new titanium chelate compounds.

DETAILED DESCRIPTION OF THE INVENTION

Specifically, this invention relates to certain chelates of titanium that are derived from reaction of a tetra-isopropyl titanate (i) with a dialkanolamine (ii) to give chelates with the general formula (iii)

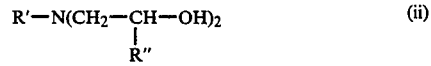

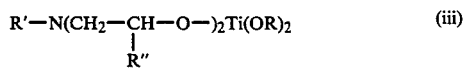

PS where R is isopropyl, R' is H, phenyl or alkyl of 1 to 10 carbon atoms and R" is H or alkyl of 1 to 6 carbon atoms and to certain hydrolysis products of the resulting chelates corresponding to formula (iv)

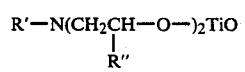

where R' and R" are the same as above. The simplest case of the invention is illustrated in Examples 1 and 2. In Example 1, tetra-isopropyl titanate (TPT) is reacted with diethanolamine (DEA) to give a clear liquid product that is designated Composition (I) and is comprised of a chelate solute in essentially two moles of functionally free isopropyl alcohol.

The chemical nature of Composition (I) and of the chelate solute derived thereof, provides the basic concept and the premise of this invention. Thus, it is important to the concept of this invention that the reaction of Composition (I) with water is rapid and highly exothermic, but gives differing products depending on the conditions of hydrolysis.

Direct contact of (I) with water or with high concentrations of water in solvent, gives insoluble and polymer-like solids that show little catalytic activity. This result of catastrophic hydrolysis is consistant with that expected from prior art concerning hydrolysis of titanium with multiple alkoxy substituents (Reference being made to Kirk-Othmar & Field & Case op cit), and with well known actions of titanate catalysts in ester manufacture where the residual catalysts are largely deactivated and precipitated from solution by hydrolysis with water or steam.

The catastrophic hydrolysis of (I) was also thought to be consistent with advantageous results disclosed in U.S. Pat. No. 4,506,091 which shows chelates to be highly effective to assist in hydrolyis of titanium catalyst residues. Further, the same assumption of debilitating effects with water was a factor in design of catalyst structures of U.S. Pat. No. 4,526,725 where isopropyl groups are replaced by higher alkyl groups to lessen water sensitivity and polymerization.

But now it has been found that hydrolysis of (I) in a judicious manner, such that water is available to the titanium in a limited manner, gives a different and highly advantageous result, providing chelate structures that appear to be effectively fully hydrolyzed yet are soluble and exhibit high activity in ester catalysis.

As shown in Example 1, a judicious hydrolysis of (I) may be accomplished by simple evaporation of the solution in a moist atmosphere, or by the addition of a very dilute solution of water in alcohol to (I) with high agitation. In each case the major product is a chelate that is crystalline in the solid state and may be re-dissolved in lower alcohols or in water. The products do not appear to change when heated in solution, but the solids decompose without melting when heated strongly above 230° C. While the hydrolyzed titanium chelates (HTC) made by either exposure to air or to wet alcohol appear to be stable, it is evident that there is a tendency for polymerization and care is required to avoid significant formation of hard materials that are insoluble in alcohol or ester reaction mixtures. Evaluation of both the solid (H-1) and the isopropanol solution (Composition II) as catalysts in standardized reactions of phthalic anhydride with 2-ethyl hexanol, conducted as in Example A, show that these products have high activity for the purpose and are essentially equivilant to Composition (I) in that regard.

Although the limited hydrolysis of (I) by the methods described in Example 1 is inconvenient to give products that are well defined and of high purity for practical use, a method has now been found that is simple, highly effective and appears to be general for other members of the series. Thus, in Example 2 the reaction of TPT with DEA that is hydrated with just one mole of water per mole of DEA gives a clear and colorless solution that is designated Composition (II) and is comprised of essentially four molecular equivalents of functionaly free isopropyl alcohol and a chelate solute (H-1) that is similar to the crystalline solids produced by exposing (I) to air, but is free of insoluble materials. It should be noted that excess of water above the 1:1 mol ratio with DEA gives insoluble gels and products that are not manageable. Evaporation of isopropyl alcohol from (II) leaves a colorless powder (H-1) in a quantity that indicates a composition equivalent to the formula: $HN(CH_2CH_2O)_2Ti-O$. The product H-1 is readily soluble in lower alcohols and dissolves in water in all proportions. Both (II) and H-1 show enhanced catalytic activity, as shown in Examples 7 and 8, and are equivalent in that respect to (I) on a contained Ti basis.

The nature of H-1 is further defined by its solubility. Solutions in water give gels at Ti concentrations above 2%. These gels readily liquify when diluted. Solutions in water appear to be highly stable in storage, and show no evidence of further hydrolysis even in boiling of the solutions. Addition of II (alcohol solution of H-1) to purified phthalate and adipate esters give rapid dissolution and precipitation of the H-1 in a very fine powder form.

For the purposes of the instant invention the nature of the hydrolyzed products (II) and H-1 may be observed in its use as catalyst for manufacture of esters. Comparison as in Examples 7, 8 and 9, and in succeeding examples, indicates that the solid H-1 and liquid (II) forms of the hydrolyzed titanium chelate are equivalent with respect to catalytic activity on an equal Ti concentration basis, and that both are essentially equivalent to the precursor Composition (I) on the same basis. Further, it is evident that (I) and (II), although having only 12.3% and 11.8% titanium, respectively, are superior to TBT (14.1% Ti) and even TPT (16.9% Ti) in catalytic activity in the 200° C. to 220° C. temperature range normally used for organometallic catalyzed esterifications. It is important to note that in reactions using equal weights of catalyst, the reaction using TPT has about 44% more titanium than the reaction using Composition II. As the reaction temperatue is lowered, the advantage of Composition (I) and especially of Composition (II) over the conventional alkoxy titanates is even larger and more significant. Comparisons at 165° C., as in Examples 14 and 15, show that (I) and (II) are more active than TPT. A reaction that requires 7 hours for completion using TPT at 165° C., as in Comparative Example B, requires less than 5 hours to complete using Composition II in an amount to give an equivalent concentration of titanium, as in Example 15.

EXAMPLE I

A 2-liter, 4-neck reaction flask fitted with thermometer, mechanical stir, addition funnel and reflux condenser was purged with nitrogen and charged with 1136 g (4 mol) of tetra-isopropyl titanate (Tyzor TPT, duPont). A molecular equivalent quantity of diethanolamine (UCC commercial grade, 424 g., 4 mol) was placed in the addition funnel and added to the agitated TPT during a period of 85 minutes while cooling to maintain a maximum kettle temperature of 65° C. After stirring an additional 30 minutes, there was discharged 1560 g of a pale yellow, oil product designated Composition I, with a density of 1.015 g/cc @20° C. Removal of free isopropyl alcohol from 79 g of Composition I by evaporation to constant weight with vacuum to 15 torr and heating with 70° C. water bath gave 52.5 g of an amber residue that cools to a clear glass at room temperature. Reaction of Composition I with water is rapid and exothermic, giving hard and insoluble gels and white polymer-like solids. Separation and use of these solids as catalyst in reaction of diethylene glycol with dimethyl glutarate shows little tendency for catalysis. In a separate experiment, a quantity of 28 g of Composition I was placed in an open dish exposed to the atmosphere and evaporated with intermittent mixing to give 13.1 g of a colorless crystalline solid which is quite different from the solids from direct hydrolysis in that it readily redissolves in alcohol and is soluble in water as well. Use of these solids as catalyst in reaction of DEG with dimethyl glutarate shows high catalytic activity. In a separate experiment, 390 g of Composition I was treated dropwise with a solution of 18 g of water in 360 g of isopropyl alcohol with vigorous agitation and cooling to maintain a maximum temperature of 60° C. Gels formed early in the reaction gradually dissolved and further gels did not form after about 40% of water was added. The amount of insoluble gel appears to depend on rate of water addition; aqueous solutions over 5% give products with insoluble gels. In this experiment there is discharged 768 g of a colorless liquid with a slight haze. Evaporation of 77 g of this liquid with a 70° C. bath and reduced pressure, gives 16.8 g of white crystalline solids that are similar in appearance, IR spectra and solubility to the solids obtained by air evaporation of Composition I. These solids are designated Composition I-H.

EXAMPLE 2

An apparatus arranged as in Example 1 was charged with 1136 g (4 mol) of tetra-isopropyl titanate (Tyzor TPT). A solution of 72 g (4 mol) of water and 424 g (4 mol) of diethanolamine (UCC) was placed in the addition funnel and added dropwise to the TPT with vigorous agitation. A small quantity of gels formed in the initial stage of reaction, but dissolved when 40% of the mixture was added. Reaction is highly exothermic and cooling was applied to control the temperature at 80° C. Addition was complete within 60 minutes and the product (Composition II) was cooled to give 1650 g of clear, colorless and oily liquid with density (20° C.) of 1.02 g/cc. A quantity of (56 g) of II was evaporated under vacuum at 60° C. to give a white crystalline solid (23.3 g) that is readily soluble in lower alkyl alcohols and water and is similar in appearance, IR, thermal decomposition and solubility characteristics to H-1 of Example 1. Composition II is miscible with water in all proportions giving gels at concentration of more than 2% titanium but reverting to solutions with dilution to lower concetration. Solutions remain clear to 100° C. (boiling).

EXAMPLE 3

A 1-liter flask fitted as in Example 1 was purged with nitrogen and charged with 284 g (1 mol) tetra-isopropyl titanate (Tyzor TPT). A solution of 135 g (1 mol) of di-isopropanolamine (Dow) mixed with 18 g (1 mol) of water and placed in the addition funnel and fed dropwise to the TIPT with rapid agitation during 30 minutes and the temperature maintained below 60' C. After cooling there was collected 437 g of a pale yellow oil (Composition III) having a density (20° C.) of 1.07 g/cc. A quantity of III (42 g) was evaporated with vacuum at 60° C. to give 18.82 g of a white crystalline product identified as H-2. Addition of water to III results in clear solutions that are stable at ambient temperature, but concentrations of more than 2% by weight of titanium gel when heated at 65° C.

EXAMPLE 4

A 1-liter flask fitted as in Example 1 was purged with nitrogen and charged with 284 g(1 mol) of tetra-isopropyl titanate (Tyzor TPT). A solution of 163 g (1 mol) of N-t-butyl diethanolamine (Pennwalt) combined with 18 g (1 mol) of water was placed in the addition funnel and added dropwise to the TIPT during a 30 minute period while maintaining the temperature below 60° C. After cooling there was collected 465 g of a viscous yellow liquid designated as Composition IV. A 23.2 g quantity of IV was placed in a flask and evacuated at 60° C. to remove volatiles, leaving 11.3 g of a yellow crystalline solid H-3. Addition of water to IV gives clear solutions to about 60% water. Water solutions of IV remain clear and liquid when heated to boiling.

EXAMPLE 5

A solution of 18.5 g (0.1 mol) of N-phenyl diethanolamine (Eastman) and 1.8 g (0.1 mol) of water was added dropwise to 28.4 g (0.1 mol) of tetra-isopropyl titanate in a 50 ml flask equipped with magnetic stir. Reaction was highly exothermic and resulted in a 2phase system comprising a bright yellow solids and a liquid comprised essentially of isopropyl alcohol. Evaporation of the alcohol with vacuum and mild heat left 24.5 g of the bright yellow solid H-4, which was found to be insoluble in water and lower alcohols, but soluble in hot decyl alcohol and melting with decomposition at 245°-260° C.

COMPARATIVE EXAMPLE A

A standard esterification apparatus, consisting of a 1-liter, 3 neck flask fitted with heating mantle, thermometer, nitrogen inlet tube and modified Dean-Stark separator topped with a total reflux condenser connected to a vacuum system, was charged with 148 g (1 mol) of phthalic anhydride, 312 g (2.4 mol) of 2-ethyl hexyl alcohol and 0.2 g (0.135% of PA charge) of tetrabutyl titanate (Tyzor TBT) catalyst. Heat was applied at a standardized setting and water of esterification began to form at a kettle temperature of 165° C. Heating was continued to reflux at 220° C. while removing water of reaction as fast as it is formed by azeotrope with toluene. Progress of reaction was monitored by rate of water formation until about 98% conversion of acid, at which time the reaction was sampled and the acid number determined by titration with 0.05N alcoholic KOH using bromthymol blue indicator. After 3.0 hours reaction time, the AN was reduced to 0.1 mg KOH/g, at which time the excess alcohol was removed by reducing the pressure of the system and removing alcohol distillate through the modified separator. Vacuum distillation was continued to 20 torr/200° C. at which time conditions were adjusted to 75 torr/150° C. and removal of alcohol continued by steam distillation, accomplished by dropwise addition of water to the bottom of the flask at a rate of about 1 ml/minute while maintaining the kettle at 150°-160° C. The kettle became cloudy after about 10 minutes. Distillation was continued for 30 minutes, at which time heat was removed and the system dried at full vacuum (12 torr) for 10 minutes. After cooling to 90° C. the cloudy residue was filtered through a No. 1 Whatman paper with a Buchner vacuum filter. The filtrate is cloudy and plugs the filter quickly. Refiltering with filter aid gives low odor di-octyl phthalate with AN=0.14 and color of 20 APHA.

EXAMPLE 6

A reaction was conducted as in Comparative Example A except that 0.2 g of Composition I was used as catalyst. After 1.8 hours reaction time 97% of the water was removed and the AN is 4.1 mg KOH/g. After 2.65 hours the AN is 0.07 mg KOH/g and alcohol was removed by vacuum and steam distillation. After drying the cloudy residue product was filtered thru a No. 1 Whatman paper. Filtration was slow but continuous to give a clear, low odor di-octyl phthalate ester with color of 15 APHA and AN=0.02 mg KOH/g.

EXAMPLE 7

A reaction was conducted as in A except that 0.2 g of Composition II was used as catalyst. After 2 hours reaction time, 98% of the water is removed the AN=1.48 mg KOH/g. After 2.7 hours the AN=0.04 mg KOH/g and alcohol was removed by vacuum and steam distillation. Cloudiness appeared after 3 minutes of steam distillation. After drying the cloudy residue was filtered thru a No. 1 paper to give a clear and low odor ester product with AN=0.04 and color of 10 APHA. Rate of filtration was slow but constant. Catalyst residues were brown and very fine particles. Washing with hexane and analysis by IR indicates presence of nitrogen and carbonyl.

EXAMPLE 8

A reaction was conducted as in Comparative Example A except that 0.25 g of the Composition H-1 was used as catalyst. After 1.75 hours reaction time all water of reaction was collected and the AN=0.02 mg KOH/g. Alcohol was removed by vacuum and steam distillation. The kettle became cloudy after only 1 minute of steam distillation and the dried residue product was very cloudy. Filtration of the ester product through a No. 1 paper gave a clear product with color of 15 APHA and AN=0.01 mg KOH/g. The solid residues from this filtration were washed with hexane to give 0.3 g of tan solids showing both nitrogen and carbonyl in IR scans.

EXAMPLE 9

A reaction was conducted as in Comparative Example A except that 0.25 g of the recovered catalyst residues from Example 8 were used as catalyst. After 2.25 hours reaction time, all of the water of reaction was collected and the AN=0.07 mg KOH/g.

EXAMPLE 10

A reaction was conducted as in Example A except that 0.2 g of Composition III was used as catalyst. After 3 hours reaction time all water of reaction was collected and the AN=0.05 mg KOH/g.

COMPARATIVE EXAMPLE B

A reaction was conducted as in Example A except the temperature of reaction was maintained at 165° C. by reducing the pressure of the system, and the catalyst charge was adjusted to 0.425 g of tetra-isopropyl titanate (Tyzor TPT). After 5.25 hours 95% of the water of reaction was collected and the AN=2.48 mg KOH/g. At the end of 7.0 hours removal of water was complete and the AN=0.08 mg KOH/g at which time the alcohol was removed by vacuum and steam distillation. The dried residue product was very cloudy had a broad range of particle size. Filtration thru a No. 1 paper gave a hazy ester with AN=0.13 mg KOH/g. the residue catalyst solids collected on the filter were washed with Hexane to give 0.25 g of a tan solid shown by IR to have a significant carbonyl content which is not reduced by further washing with hexane.

EXAMPLE 11

A reaction was conducted as in Comparative Example B except that 0.425 g of Composition II was used as catalyst. After 5 hours, 93% of the water of reaction was collected and the AN=3.1 mg KOH/g. At the end of 6.75 hours all of the water was collected and the AN=0.06 mg KOH/g. Excess alcohol was removed by vacuum and steam distillation giving a cloudy residue product which was filtered thru a No. 1 paper to give a clear ester with color of 15 APHA and AN=0.04 mg KOH/g. The recovered catalyst solids were washed with hexane to give 0.17 g of brown solids that decompose above 230° C. with loss of vapor basic to litmus paper.

EXAMPLE 12

A reaction was conducted as in Example 11 except that the catalyst change was adjusted to 0.63 g of II to give a titanium concentration equivalent to that of Comparative Example B. At the end of 4.6 hours all water of reaction was collected and the AN=0.03 mg KOH/g., at which time alcohol was removed by vacuum and steam distillation and the product filtered thru a No. 1 paper giving a clear ester with color of 20 APHA and AN=0.04 mg KOH/g and 0.25 of brown catalyst residues.

EXAMPLE 13

A quantity of Composition II was placed in a tube and mixed dropwise with the amount of water shown. Time for gelation is listed along with appearance. Tubes were maintained at 25° C.

| Sample | Wt. II, g. | Wt. Water g | Gel Time, min. | |
|---|---|---|---|---|
| a | 4 | 4 | 0.5 | clear, dry gel |
| b | 3 | 6 | 0.75 | clear, dry gel |
| c | 2 | 6 | 2.0 | clear, rubbery gel |
| d | 2 | 8 | 3.5 | clear, soft gel |
| e | 2 | 10 | 10 | clear, wet gel |
| f | 2 | 12 | 10+ | clear, vis. liquid* |
| g | 2 | 14 | — | clear liquid** |

*Liquid stable in storage 30 days
**Liquid stable in storage 6 months

A quantity of Composition III was placed in a tube and mixed cropwise with the amount water shown. Tubes were heated in an 85° C. water bath. Temperature of gelation is listed along with appearance.

| Sample | Wt. III g. | Wt. Water g | Gel Temp. C. | |
|---|---|---|---|---|
| a | 5 | 6.5 | 56-58 | clear, dry gel |
| b | 5 | 9.75 | 60-65 | cloudy, soft gel |
| c | 5 | 13 | 65-68 | cloudy, viscous liq. |

I claim:

1. Compositions which are the reaction products of essentially molecular equivalent quantities of a tetra-isopropyl titanate, (i) Ti(OR)$_4$ and a dialkanolamine $$R'-N(CH_2-CH-OH)_2 \quad \text{(ii)}$$
$$\phantom{R'-N(CH_2-}|\phantom{CH-OH)_2}$$
$$\phantom{R'-N(CH_2-}R''$$

where R is isopropyl, R' is H, phenyl or alkyl of 1 to 10 carbon atoms and R" is H or alkyl of 1 to 6 carbon atoms, and said reaction products consist of free isopropyl alcohol and a titanium chelate adduct which is catalytically active and chemically reactive in a manner consistent with the functionality represented by structure, $$R'-N(CH_2-CH-O-)_2Ti(OR)_2 \quad \text{(iii)}$$
$$\phantom{R'-N(CH_2-}|$$
$$\phantom{R'-N(CH_2-}R''$$

2. Compositions which are hydrolysis products and which consist of the compositions of claim 1 combined with one molecular equivalent of water in a manner that the resultant composition has essentially 4 molecular equivalents of functionally free isopropyl alcohol, and a reaction product which exhibits chemical characteristics consistent with funtionality represented by structure (iv)

$$R'-N(CH_2CH-O-)_2TiO$$
$$\phantom{R'-N(CH_2}|$$
$$\phantom{R'-N(CH_2}R''$$

and which exhibit a high level of catalytic activity.

3. Compositions of claim 2 wherein the manner of manufacturing the compositions consists of mixing the tetra-isopropyl titanate with a solution comprised of the appropriate molecular equivalent quantities of the dialkanolamine and water.

4. Compositons of claim 3 wherein all or part of the functionally free isopropyl alcohol is removed.

5. Compositions of claim 3 where all or part of the functionally free alcohol is replaced by other solvents or mixtures of solvents, said solvents being selected from the group of alcohols and water that can individually or in mixture thereof dissolve and maintain solution of the residues represented by structure $$R'-N(CH_2CH-O-)_2TiO \quad \text{(iv)}$$
$$\phantom{R'-N(CH_2}|$$
$$\phantom{R'-N(CH_2}R''$$

said alcohols being selected from the group of alkyl alcohols of 1 to 13 carbon atoms, alkylene diols of 2 to 8 carbon atoms di-ethylene glycol and di-propylene glycol.

* * * * *